United States Patent [19]

Leonard

[11] Patent Number: 4,936,411
[45] Date of Patent: Jun. 26, 1990

[54] DETECTABLE EARPLUG

[75] Inventor: David A. Leonard, Macclefield, England

[73] Assignee: Cabot Corporation, Waltham, Mass.

[21] Appl. No.: 234,427

[22] Filed: Aug. 19, 1988

[51] Int. Cl.$^5$ .............................................. A61B 7/02
[52] U.S. Cl. .................................... 181/135; 181/130; 128/864
[58] Field of Search ...................... 181/129, 130, 135; 128/864–868; 340/568, 572

[56] References Cited

U.S. PATENT DOCUMENTS

| | | | |
|---|---|---|---|
| 4,219,018 | 8/1980 | Draper, Jr. | 128/864 |
| 4,314,553 | 2/1982 | Westerdal | 187/135 X |
| 4,682,154 | 7/1987 | Fearon et al. | 340/572 |

FOREIGN PATENT DOCUMENTS 0244979 11/1987 European Pat. Off. .

Primary Examiner—Benjamin R. Fuller
Attorney, Agent, or Firm—Buchanan Ingersoll; Lynn J. Alstadt

[57] ABSTRACT

A molded detectable earplug assembly includes a pair of earplugs into which a metal, magnetic or X-ray detectable insert is provided. Preferably the earplugs are in pairs connected by a cord. The metal, magnetic or X-ray detectable sphere is detectable by metal, magnetic or X-ray detecting equipment and will announce the presence of an earplug in a product which was processed in a food, beverage, tobacco, or pharmaceutical processing line.

17 Claims, 1 Drawing Sheet

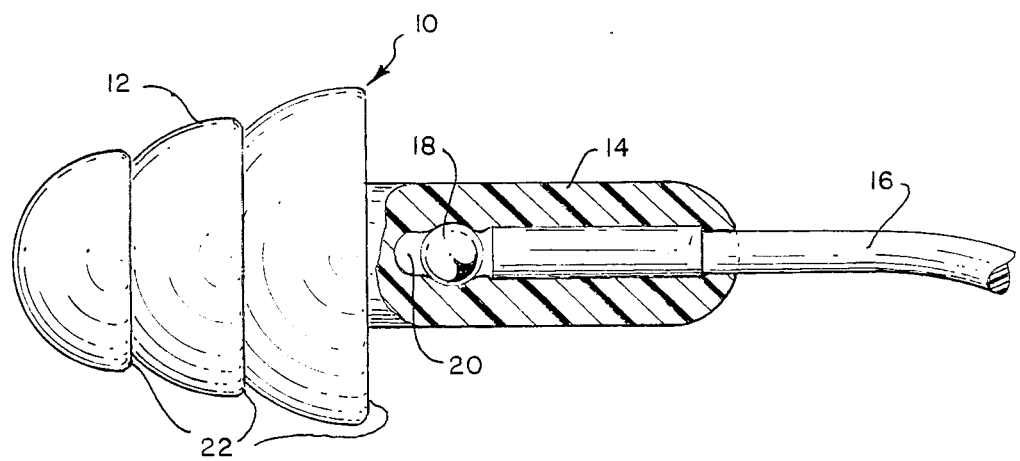

DETECTABLE EARPLUG

BACKGROUND OF THE INVENTION

1. Field of the Invention

This invention relates to molded earplugs and, more particularly, to molded earplugs which are easily detectable by X-rays or other scanning methods.

2. Background of the Prior Art

Earplugs and other hearing protectors have become standard equipment in many industries where there is continuous exposure to the excessive noises generated by manufacturing or processing equipment. These earplugs and hearing protectors provide inumerable benefits to the employees working in the processing line and reduce health-related costs to the employer. However, the taking of foreign objects such as earplugs into certain process areas is not without risk. When used on a food or beverage processing line, a pharmaceutical line, or any other processing line where there is exposure to consumable items, there is a risk that an earplug may fall into the foodstuff, beverage, pharmaceutical, or other substance being processed. Although these processing lines are invariably provided with detectors of a sort for detecting metallic objects, earplugs which are made of a foam material, soft rubber, or plastic cannot be detected by such safety systems.

In order to prevent the earplug from falling into the foodstuff, it has been the practice to provide a pair of earplugs on opposite sides of a length of cord. In this instance, if one earplug becomes loose, it will remain retained on the end of the length of cord. It will not fall into the foodstuffs on the processing line. However, it is possible for the cord to become separated from the earplug and the earplug to become dislodged from the ear of its wearer. In such an instance, the earplug could fall into the foodstuff and would not be detected by normal detection means.

To remedy the risk of a nondetectable earplug falling into the foodstuffs on a processing line, Salmon, European Patent Publication No. 244 979, teaches the use of a metal ferrule provided on the end segments of the length of cord for use in a corded earplug. The metal ferrule is forced into the earplug so that the ferrule is wholly contained within the plug. Because the metal ferrule is crimped onto the cord, Salmon claims that it is very unlikely that the length of cord will ever become detached from the ferrule.

Although an improvement over the prior corded earplugs, the Salmon earplugs are nevertheless confronted with deficiencies. First, the metal ferrule requires a particular material for the cord composition. A PVC or other plastic cord which does not transmit noise to the extent that an ordinary cord does is not compatible with the metal ferrule. If the metal ferrule were placed on the ends of a PVC or other plastic cord, there is a much greater possibility of the cord separating from the plug. Second, should the cord and earplug separate, the chances are great that the detectable part of the product, that being the metal ferrule, will remain on the cord. As a result, the employee on the line is left with a loose undetectable plug which could fall into the foodstuff. Finally, the use of the metal ferrule in the earplug limits the flexibility of the earplug. This hinders the insertion of the earplug into the wearer's ear as well as causing a degree of discomfort to the wearer during normal wear.

SUMMARY OF THE INVENTION

I provide a metallized molded earplug which provides assurance to the food, beverage, tobacco, and pharmaceutical industries that lost earplugs will not be processed. A pair of earplugs are provided with a detectable insert located in the stem of each earplug. The detectable insert can be formed of any metal that is detectable by conventional metal detecting equipment. Alternatively, a magnetic insert or X-ray detectable insert may be used. Preferably, the detectable insert is a sphere. A cord is provided which attaches to the stems of each earplug. As is common for non-detectable corded earplugs I prefer to use a PVC or other plastic cord to attach the earplugs. The same or similar procedures as are used to attach cords to nondetectable corded earplugs can be used for my detectable earplug. A PVC or other plastic cord is used because it does not transmit noise to the extent that an ordinary cord does. PVC and other plastic cords have an external surface that is free of fibers that cause friction.

If separation of the cord from an earplug does occur, the loose plug remains detectable. Because the detectable part of my earplug is and will remain in the earplug, some may wish to use my product without a cord. This is an improvement over the Salmon earplug wherein the detectable part of the product remains on the cord leaving a loose undetectable plug.

A final advantage of the present earplug is that the detectable insert can be made much smaller than the metal ferrule of the Salmon earplug. Particularly when the detectable insert is a sphere, the flexibility of the stem of the earplug is not restricted. This provides an earplug which could be easily inserted and removed from the ear of the wearer. Furthermore, the earplug will not create any discomfort to the wearer as a result of the presence of the detectable insert.

BRIEF DESCRIPTION OF THE DRAWING

The FIGURE is a side view partially in section of a present preferred embodiment of a detectable molded earplug according to the present invention.

DESCRIPTION OF THE PREFERRED EMBODIMENT

As shown in the FIGURE, detectable molded earplug 10 includes earplug 12 having stem portion 14. Cord 16 is connected at its end to earplug 12. This connection can be made by a friction fit, gluing or ultrasonic bonding. A detectable insert 18 is provided within a channel 20 located in the stem 14 of earplug 12.

Preferably, earplug 12 is an ULTRAFIT earplug manufactured by Cabot Corporation having a plurality of flanges 22 having continuous curved cups that overlap each other. However, any type of earplug can be used in accordance with the present invention.

Detectable insert 18 is preferably in the form of a sphere and is inserted into channel 20 of stem 14 of earplug 12 before cord 16 is attached thereto. However, detectable insert 18 can be formed in any shape which does not cause discomfort to the earplug wearer or hinder the insertion or removal of the earplug 12 from the ear. Detectable insert 18 and cord 16 remain independent of each other. If cord 16 separates from earplug 12, detectable insert 18 remains within earplug 12. In this manner, the detectable portion of earplug 10 always remains within earplug 12.

Detectable insert 18 may be formed of any metal that is detectable by conventional metal detecting equipment. Currently, the food, beverage, tobacco, and pharmaceutical industries utilize X-rays, metal detectors, and similar scanning means to detect the presence of foreign objects in their foodstuffs or other consumable items. Consequently, detectable insert 18 should be formed of a material that will be detected by this same equipment. If an earplug of the sort described herein becomes dislodged from the ear and is deposited into the foodstuff or other consumable item, the package containing the earplug can be readily located, thereby prevent disruption and possible product loss.

While I have described certain presently preferred embodiments of my invention, it is to be distinctly understood that the invention is not limited thereto and may be otherwise variously practiced within the scope of the following claims.

I claim:

1. A detectable earplug assembly comprising
   (a) a pair of earplugs, each of said earplugs of a size and shape adapted to be inserted into and obturate an ear canal and having a channel extending into said earplug, said channel having a diameter of sufficient size to accommodate a detectable insert;
   (b) said detectable insert having a diameter large enough so that said insert will be restricted from coming out of the channel during normal use, the detectable insert being comprised of a material which is detectable by scanning means and having a size and shape which does not hinder insertion and removal of the earplug; and
   (c) a cord connecting each of said earplugs, said cord attached at each end thereof to one of said earplugs through insertion into said channel of each earplug after placement of said detectable insert in said channel, and said cord being independently connected such that if said cord is separated from said earplugs said insert will remain in said channel of said earplug.

2. The earplug assembly of claim 1 wherein said cord is a plastic cord.

3. The earplug assembly of claim 1 wherein said cord is a PVC cord.

4. The earplug assembly of claim 1 wherein said detectable insert is composed of a metal which is detectable by metal detecting equipment.

5. The earplug assembly of claim 1 wherein said detectable insert is composed of a magnetic material.

6. The earplug assembly of claim 2 wherein said detectable insert is composed of an X-ray detectable material.

7. The earplug assembly of claim 1 wherein said detectable insert is in the shape of a sphere.

8. The earplug assembly of claim 1 wherein each of said earplugs has an elongated stem from which a plurality of flanges project outward, said flanges having continuous curved cups that overlap each other.

9. The earplug assembly of claim 8 wherein said channel is provided in said stem and said detectable insert is inserted in to channel of the stem of each of said earplugs and said cord attaches to said stem of each of said earplugs.

10. A detectable earplug comprising an earplug body having a size and shape adapted to be inserted into and obturate an ear canal of a wearer having a channel extending into said earplug, said channel having a diameter of sufficient size to accommodate separate and unattached detectable insert and connecting cord inserted a detectable insert in said earplug body, said insert having a diameter large enough so that said insert will be restricted from coming out of said channel during normal use, the detectable insert being comprised of a material which is detectable by scanning means and having a size and shape which does not cause discomfort to the wearer and does not hinder insertion and removal of the earplug.

11. The detectable earplug of claim 10 wherein said detectable insert is composed of a metal which is detectable by metal detecting equipment.

12. The detectable earplug of claim 10 wherein said detectable insert is composed of a magnetic material.

13. The detectable earplug of claim 10 wherein said detectable insert is composed of an X-ray detectable material.

14. The detectable earplug of claim 10 wherein said detectable insert is in the shape of a sphere.

15. The detectable earplug of claim 14 wherein said earplug body has an elongated stem from which a plurality of flanges project outward, said flanges having continuous curved cups that overlap each other.

16. The detectable earplug of claim 15 wherein said channel is provided in said stem and said detectable insert is inserted in said channel of said stem of said earplug body.

17. The detectable earplug of claim 15 wherein said channel is provided axially in said stem of said earplug body, said channel adapted to receive an end portion of said cord and secure said end portion therein.

* * * * *

UNITED STATES PATENT AND TRADEMARK OFFICE
CERTIFICATE OF CORRECTION

PATENT NO. : 4,936,411

DATED : June 26, 1990

INVENTOR(S) : DAVID A. LEONARD

It is certified that error appears in the above-identified patent and that said Letters Patent is hereby corrected as shown below:

Column 3, line 24, claim 1, after "canal" insert --of a user--.

Column 4, line 17, claim 10, after "wearer" insert --and--.

Column 4, line 19, claim 10, after "accommodate" insert --a--.

Signed and Sealed this

Tenth Day of September, 1991

Attest:

HARRY F. MANBECK, JR.

*Attesting Officer*  *Commissioner of Patents and Trademarks*